United States Patent [19]
Katsuda et al.

[11] 4,161,537
[45] Jul. 17, 1979

[54] INSECTICIDAL ISOVALERIC ACID ESTERS

[75] Inventors: Yoshio Katsuda, Nishinomiya; Minoru Nakajima; Toshio Fujita, both of Kyoto, all of Japan

[73] Assignee: Dainippon Jochugiki Kabushiki Kaisha, Osaka, Japan

[21] Appl. No.: 856,207

[22] Filed: Nov. 30, 1977

[51] Int. Cl.² .............. A01N 9/20; C07C 101/00; C07C 121/75
[52] U.S. Cl. .............. 424/304; 260/465 D; 260/544 N; 260/546; 560/43; 562/433; 562/456; 424/309
[58] Field of Search .............. 260/465 D; 560/43; 424/304, 309

[56] References Cited
U.S. PATENT DOCUMENTS 4,056,628  11/1977  Winternize .............. 424/308

Primary Examiner—Dolph H. Torrence
Attorney, Agent, or Firm—Brisebois & Kruger

[57] ABSTRACT

Isovaleric acid ester derivatives and the optical isomers thereof expressed by the general formula I:

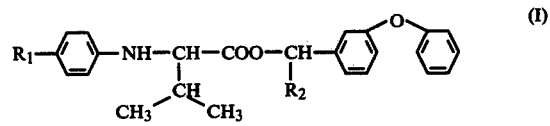

wherein,
$R_1$ represents hydrogen, methyl group or chlorine atom, and
$R_2$ represents hydrogen or cyano group.

21 Claims, No Drawings

INSECTICIDAL ISOVALERIC ACID ESTERS

This application is related to Japanese Patent Application Numbers Sho 50-147601, Sho 51-144992, Sho 51-149079, Sho 52-20733, Sho 52-33479 and Sho 52-37828.

DETAILED EXPLANATION OF THE INVENTION

The present invention relates to novel isovaleric acid ester derivatives and the optical and geometrical isomers thereof, a process for producing said derivatives and insecticides containing as active ingredient said derivatives of the general formula I:

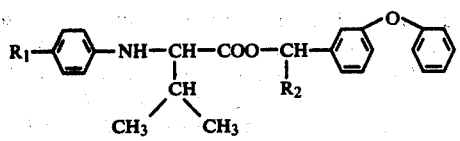

wherein, $R_1$ represents, hydrogen, methyl group or chlorine atom, and $R_2$ represents hydrogen or a cyano group.

Various alcohol components of cyclopropane carboxylic acid esters have been investigated and the esters are practically used. However, the compounds are easily decomposed by light and therefore the outdoor use of these compounds is restricted.

As the result of recent investigations on acid components of the esters, more stable compounds to light than the conventional pyrethroids have been produced by substituting methyl group into halogen atom. However, taking the environmental pollution and chronic toxicity into consideration, insecticides having similar structure as those of natural organic compounds consisting of carbon, hydrogen, oxygen and nitrogen will be advantageously used in the future. The present inventors have intensively investigated on insecticides and found that the compound of the general formula (I) showed remarkably strong insecticidal action against various sanitary and agricultural pests, while it is more stable to light than the conventional pyrethroids and is very low toxic against warm blooded animals.

Thus, the present invention is accomplished based on the knowledge mentioned above. The compound of the formula (I) used as active ingredient in the present invention can be produced according to the ordinary processes for producing esters by reacting a carboxylic acid or a reactive derivative thereof having the general formula IV:

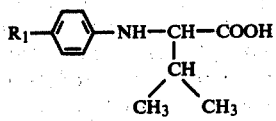

wherein, $R_1$ represents, hydrogen, methyl group or chlorine atom, with an alcohol or a reactive derivative thereof having the formula V:

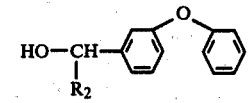

wherein $R_2$ represents hydrogen or a cyano group.

Reactive derivatives of carboxylic acid are, for example, acid halides, acid anhydrides, lower alkyl esters and alkali metal salts. Reactive derivative of alcohol is, for example, chloride. The reaction is carried out in a suitable solvent in the presence of organic or inorganic base, or acid as deacidificating agent or catalyst, if desired, and at elevated temperature at need. Representative compounds of the formula (I) are as follows:

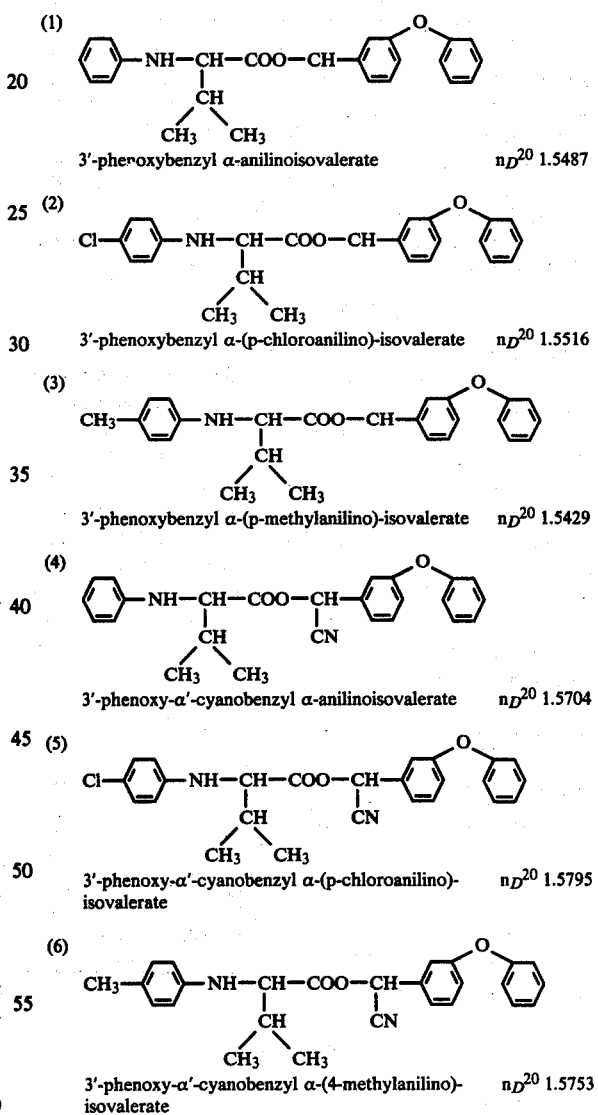

The compounds of the present invention which are novel one are solid or liquid at room temperature and usually easily soluble in organic solvent. Accordingly, they may be used as ingredients in insecticidal sprays in the form of emulsion, solution, powder, wettable powder and aerosol etc. In addition, they may be used as insecticides for fumigation by mixing them with some appropriate substrate such as powdered wood and making mosquito incense sticks. Furthermore, these compounds show also strong effect as mosquito incense sticks when they are employed as insecticides for heating and evaporating use. Namely, they are dissolved in a suitable organic solvent and the solution is absorbed into a carrier and then the resulting product is heated on an appropriate heater. As the compounds of the present invention are more stable to light than the conventional pyrethroids, they may be used as agricultural insecticides.

Addition of some synergists into the compounds, for example, N-octylbicycloheptene dicarboxyimide (MGk-264 is the commercial name), a mixture composed of N-octylbicycloheptene dicarboxyimide and alkylarylsulfonic acid salt (MGK-5026 is the commercial name), octachlorodipropylether, or pyperonylbutoxide, can enhance the insecticidal effect.

The stability of this compound can be increased by adding some phenolic- or amine-antioxidants such as 2,6-di-tert-butyl-4-methylphenol (BHT), 2,6-di-tert-butylphenol and the like. More highly active insecticides can be obtained by joint use of the compounds with the conventional pyrethroids such as allethrin, phthalthrin, resmethrin and furamethrin.

In the following, test results on the insecticidal effect of the compounds used as active ingredients are given.

TEST EXAMPLE 1

Insecticidal effect by spraying test

With respect to each 0.2% white kerosene solution of 6 compounds of the present invention which are exemplified above (A), a white kerosene solution containing 0.2% of each compound of the present invention and 0.8% of pyperonylbutoxide (B), a white kerosene solution containing 0.1% of each compound of the present invention and 0.1% of phthalthrin (C), a 0.2% white kerosene solution of allethrin and a 0.2% white kerosene solution of phthalthrin, the relative effect values were estimated from the knockdown rate of house flies by spraying and the mortality after 24 hours was obtained as follows:

| Test preparation | (A) | (B) | (C) |
|---|---|---|---|
| Allethrin | 1.00 (26) | — | — |
| Phthalthrin | 2.15 (34) | — | — |
| (1) | 1.23 (84) | 1.67 (100) | 1.59 (90) |
| (2) | 2.02 (100) | 2.15 (100) | 2.38 (100) |
| (3) | 2.15 (100) | 2.19 (100) | 2.27 (100) |
| (4) | 1.77 (100) | 2.24 (100) | 2.02 (100) |
| (5) | 1.98 (100) | 2.30 (100) | 2.14 (100) |
| (6) | 2.03 (100) | 2.36 (100) | 2.28 (100) |

The parenthesized values show the mortality after 24 hrs.

TEST EXAMPLE 2

Insecticidal effect by fumigation test

Mosquito incense sticks containing each 0.5% active ingredient were prepared and tested for the knockdown rate of red house mosquitoes. These tests were carried out in accordance with the procedure described by Nagasawa, Katsuda and others in "Bochu-Kagaku" Vol. 16, page 176 (1951). The test numbers of the active ingredients are the same as those of Example 1. The relative effect values of these mosquito incense sticks are as follows:

| Test preparation | Probit 4 | Probit 5 | Probit 6 |
|---|---|---|---|
| Allethrin | 1.00 | 1.00 | 1.00 |
| (1) | 1.30 | 1.35 | 1.40 |
| (2) | 1.34 | 1.37 | 1.39 |
| (3) | 1.62 | 1.65 | 1.70 |
| (4) | 1.46 | 1.49 | 1.52 |
| (5) | 1.58 | 1.61 | 1.64 |
| (6) | 1.61 | 1.65 | 1.69 |

The compounds according to the present invention are exemplified in the following. The name of the compound is the same as mentioned in the examples of active ingredient shown above.

EXAMPLE 1

A solution of 5.0 g of α-(4-chloroanilino)isovaleryl chloride in 15 ml of dry benzene was mixed with a solution of 4.7 g of 3-phenoxy-α-cyanobenzylalcohol in 20 ml of dry benzene. When 3 ml of dry pyridine were added into the solution as promotor of the condensation, crystals of pyridine hydrochloride were precipitated. The mixture was allowed to stand in a tightly stopped vessel for one night and the pyridine hydrochloride was filtered off. The filtrate was dried over sodium sulfate and benzene was distilled off under reduced pressure to yield 7.5 g of 3'-phenoxy-α'-cyanobenzyl α-(4-chloroanilino)-isovalerate.

EXAMPLE 2

2.0 g of α-anilinoisovaleric acid and 1.9 g of 3-phenoxybenzyl alcohol were dissolved in 150 ml of benzene and 5 ml of concentrated hydrochloric acid were added into the solution with vigorously stirring. The mixture was refluxed with stirring and water distilled by azeotropy was removed with dehydrating agent. The reaction was continued for about 4 hrs. with supplying benzene at need.

Then the reaction mixture was washed with an aqueous solution of sodium hydrogencarbonate and with an aqueous solution of sodium chloride. Benzene was distilled off under reduced pressure to yield 3.1 g of 3'-phenoxybenzyl α-anilinoisovalerate.

EXAMPLE 3

4.5 g of sodium α-(4-chloroanilino)-isovalerate and 4.5 g of 3-phenoxybenzylchloride were dissolved in 50 ml of benzene and the mixture was heated under reflux in nitrogen atmosphere for 3 hrs.

The reaction mixture was cooled and crystals of sodium chloride precipitated were filtered off. The filtrate was thoroughly washed with aqueous solution of sodium chloride and dried over sodium sulfate. Benzene was distilled off under reduced pressure to give 6.8 g of 3'-phenoxybenzyl α-(4-chloroanilino)-isovalerate.

EXAMPLE 4

A mixture of 4.4 g of methyl α-(4-methylanilino)-isovalerate and 4.4 g of 3-phenoxy-α-cyanobenzyl alcohol was heated at 150° C. When the temperature of the mixture reached to 150° C., 0.25 g of sodium was added to start distillation of methanol. Further 0.25 g of sodium was added into the mixture when distillation of methanol ceased while keeping the temperature of 150° C. The procedure mentioned above was repeated until theoretical amount of methanol was distilled off. Then, the reaction mixture was cooled and dissolved in ether.

The ethereal solution was washed with diluted hydrochloric acid, aqueous solution of sodium hydrogencarbonate and aqueous solution of sodium chloride and dried over sodium sulfate. Ether was distilled off under reduced pressure to yield 7.7 g of 3'-phenoxy-α'-cyanobenzyl α-(4-methylanilino)-isovalerate.

EXAMPLE 5

7.4 g of α-anilino-isovaleric anhydride and 4.6 g of 3-phenoxy-α-cyanobenzyl alcohol were mixed and 8 g of 98% sulfuric acid was gradually added into the mixture. After conducting the reaction at 80°–100° C. for 3 hrs, the reaction mixture was dissolved in ether. The ethereal solution was thoroughly washed with aqueous solution of sodium hydrogen carbonate and then with aqueous solution of sodium chloride and dried over sodium sulfate. Ether was removed under reduced pressure to yield 7.3 g of 3'-phenoxy-α'-cyanobenzyl α-anilino-isovalerate.

EXAMPLE 6

Into a solution of 3.9 g α-(4-methylanilino)-isovaleric acid in 50 ml of dimethylformamide were added 5.4 g of 3-phenoxybenzylbromide. 4 ml of triethylamine were added into the mixture with stirring and the reaction was carried out at 60°–80° C. for 3 hrs. The reaction mixture was dissolved into ether and the ethereal solution was thoroughly washed with aqueous solution of sodium hydrogen carbonate and then with aqueous solution of sodium chloride. After drying the solution over sodium sulfate, ether was removed under reduced pressure to yield 7.2 g of 3'-phenoxybenzyl α-(4-methylanilino)-isovalerate.

REFERENCE EXAMPLE 1

Each 0.2 parts of Compounds (1), (2), (3) and (5) of the present invention is dissolved in sufficient white kerosene to form 100 parts of 0.2% solution.

REFERENCE EXAMPLE 2

Each 0.2 parts of Compounds (2), (5) and (6) of the present invention and 0.8 parts of pyperonylbutoxide are dissolved in sufficient white kerosene to form 100 parts of solution.

REFERENCE EXAMPLE 3

Each 20 parts of Compounds (1), (2), (5) and (6) of the present invention, 10 parts of Solpol SM-200 (Tradename of Toho Chemical Co.) and 70 parts of xylene were mixed with stirring to form 20% emulsion.

REFERENCE EXAMPLE 4

Each 0.4 parts of Compounds (1), (4) and (6) of the present invention, 0.1 part of resmethrin and 1.5 parts of octachlorodipropyl ether are dissolved in 28 parts of rectified kerosene. The solution is charged in an aerosol vessel and a jet-valve is attached to the vessel, through which 70 parts of propellant (liquidized natural gas) are compressed into the vessel to obtain an aerosol preparation.

REFERENCE EXAMPLE 5

Each 0.5 g of Compounds (1), (3) and (4) of the present invention and 0.5 g of BHT are uniformly mixed with 99.0 g of substrate for mosquito incense sticks such as pyrethrum extract powder, powdered wood and starch etc. The resulting substance is molded into mosquito incense stick by a publicly known process.

REFERENCE EXAMPLE 6

Each 0.4 g of Compounds (1), (3) and (6) of the present invention and 1.0 g of MGK-5026 are uniformly blended with 98.6 g of substrate for mosquito incense stick. The resulting substance is molded into mosquito incense stick by a publicly known process.

REFERENCE EXAMPLE 7

Each 3 parts of Compounds (2), (5) and (6) of the present invention and 97 parts of clay are blended and pulverized to obtain 3% powder.

REFERENCE EXAMPLE 8

Each 40 parts of Compounds (2), (3), (5) and (6) of the present invention, 35 parts of diatomaceous earth, 20 parts of clay, 3 parts of laurylsulfonic acid salt and 2 parts of carboxymethylcellulose are crushed and blended to form wettable powder.

REFERENCE EXAMPLE 9

Each 20 parts of Compounds (2), (3), (4), (5) and (6) of the present invention, 20 parts of pyperonyl butoxide, 10 parts of solpol SM-200 (Tradename of Toho Chemical Co.; emulsifier) and 50 parts of xylene were mixed with stirring to form 20% emulsion.

TEST EXAMPLE 3

Each 10 larvae at the third stage of tobacco cutworm (*Prodenia litura Fabricius*) were placed in a tall glass vessel and 1 ml portion of 1/200 diluted solution of emulsion each containing Compounds (1), (2), (3), (4), (5) and (6) of the present invention and prepared by the same procedure as in Reference Example 3 was sprayed on the larvae. Then the larvae were transferred into another glass vessel in which feed were previously placed. After 2 days, more than 80% of the larvae of tobacco cutworm in each case were killed.

TEST EXAMPLE 4

Each emulsion containing Compounds (1), (2), (3), (4), (5) and (6) of the present invention, which was prepared by the method mentioned in Reference Example 3, was diluted with water to prepare 1/200 solution. 100 1/tan (0.245 acre) of the solution was sprayed onto Japanese radish leaves at the 5–6 leaf stage, on which a lot of green peach aphid (*Myzus persicae Sulzer*) was grown all over the surface. After 2 days, the green peach aphides decrease to less than 1/10 in each case when compared to those before spraying.

TEST EXAMPLE 5

In a Wagner pot of 1/50,000 were planted rice-plants which grew for 45 days after seeding. Each wettable powder containing Compounds (1), (2), (3), (4), (5) and (6) of the present invention, which was prepared by the method mentioned in Reference Example 8 was diluted with water to prepare 1/400 solution. Each 10 ml/pot of the solution was sprayed onto the rice plants. Each 20 adult smaller brown planthoppers (*Laodelphax striatellus Fallén*) were put into the pot which was covered with a cylindrical metal net. After 1 day, more than 80% of the smaller brown planthopper were killed in each case.

TEST EXAMPLE 6

Cotton plants which have grown in a seed-plot were sprayed with each 20 ml of aqueous emulsion containing Compounds (1)–(6) of the present invention which was obtained by the method of Reference Example 9 in such amount that the active ingredient was 2 mg per one plant (about 0.2 kg/ha). On the second day and the fifth day after spraying, each 12 leaves were taken from the cotton plants from which a piece of leaf of 3.7 cm diameter was cut out. In a glass vessel of 9 cm diameter were placed a sheet of wet filter paper on which 4 leaves prepared above were put in and 5 boll weevils were settled.

Mortality of each compound tested after 72 hrs is listed as follows:

σ

| Preparation | Day after spraying | |
| --- | --- | --- |
| | 2 days | 5 days |
| Methylparathion | 13 (%) | 20 (%) |
| (1) | 90 | 75 |
| (2) | 95 | 80 |
| (3) | 95 | 80 |
| (4) | 95 | 90 |
| (5) | 100 | 100 |
| (6) | 100 | 95 |

TEST EXAMPLE 7

Each wettable powder containing Compounds (2), (3), (5) and (6) of the present invention, which was prepared by the method mentioned in Reference Example 8, was diluted with water to prepare 1/2000 solution. Cabbage leaves were thoroughly sprayed with the diluted solution obtained above. After the coating was dried, the leaves were placed in a polyethylene plastic vessel with sand and 10 cabbage army worms (*Mamestra brassicae Linne*) were settled on the cabbage leaves.

After 2 days, more than 80% of the worms were killed in each case.

TEST EXAMPLE 8

One day before applying insecticide, about 200 aphides (*Aphis craccivora Koch*) were put on each broad bean plant (*Vicia faba L*) in a pot. Each emulsion containing Compounds (1), (2), (5) and (6) of the present invention, which has been prepared by the method of Reference Example 9 was diluted with water to prepare 1/4000 solution. Each 10 ml/pot of the diluted solution was sprayed on the bean leaves which have swarmed with aphides by means of compressed air spray. After two days, any increase of damage was not observed in each case.

TEST EXAMPLE 9

Each Emulsion containing Compounds (1), (2), (4), (5) and (6) of the present invention, which was prepared by the method in Reference Example 3 and Reference Example 9 was diluted with water to prepare 1/2000 solution. Cabbage leaves were immersed in the solution for about five seconds. After the coating is dried, the leaves were put in a glass vessel in which 10 larvae of cabbage army worm were settled. The larvae were supplied twice at the date when the test leaves were prepared and 5 days after that date. Mortality of Compounds tested after 24 hrs is listed as follows:

| Preparation | Reference Example 3 | | Reference Example 9 | |
| --- | --- | --- | --- | --- |
| | first day | 5th day | first day | 5th day |
| Salithion | 40 (%) | 5 (%) | 45 (%) | 5 (%) |
| (1) | 70 | 60 | 90 | 85 |
| (2) | 75 | 60 | 95 | 85 |
| (4) | 85 | 65 | 95 | 85 |
| (5) | 85 | 75 | 100 | 95 |
| (6) | 85 | 65 | 100 | 90 |

From the above results, it is clear that the samples mixed with pyperonylbutoxide have the better effect at the first day and the five days later and the use of synergists enhances the effect of the Compounds of the present invention.

What is claimed is:

1. Isovaleric acid ester derivatives and the optical isomers thereof expressed by the general formula I:

$$R_1-\langle\text{phenyl}\rangle-NH-CH(-CH(CH_3)_2)-COO-CH(R_2)-\langle\text{phenyl}\rangle-O-\langle\text{phenyl}\rangle \quad (I)$$

wherein, $R_1$ represents hydrogen, methyl group or chlorine atom, and $R_2$ represents hydrogen or cyano group.

2. Isovaleric acid ester derivatives and the steric isomers thereof according to claim 1, which are expressed by the general formula II:

$$R_1-\langle\text{phenyl}\rangle-NH-CH(-CH(CH_3)_2)-COO-CH_2-\langle\text{phenyl}\rangle-O-\langle\text{phenyl}\rangle \quad (II)$$

wherein $R_1$ represents the same meaning given in claim 1.

3. Isovaleric acid ester derivatives and the steric isomers thereof according to claim 1, which are expressed by general formula III:

$$R_1-\langle\text{phenyl}\rangle-NH-CH(-CH(CH_3)_2)-COO-CH(CN)-\langle\text{phenyl}\rangle-O-\langle\text{phenyl}\rangle \quad (III)$$

wherein $R_1$ represents the same meaning given in claim 1.

4. Compound according to claim 2 having the formula:

$$\langle\text{phenyl}\rangle-NH-CH(-CH(CH_3)_2)-COO-CH_2-\langle\text{phenyl}\rangle-O-\langle\text{phenyl}\rangle$$

5. Compound according to claim 2 having the formula:

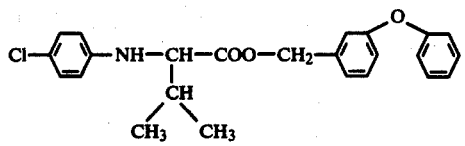

6. Compound according to claim 2 having the formula:

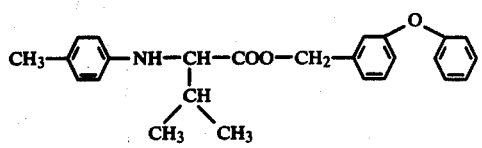

7. Compound according to claim 3 having the formula:

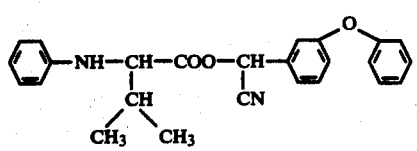

8. Compound according to claim 3 having the formula:

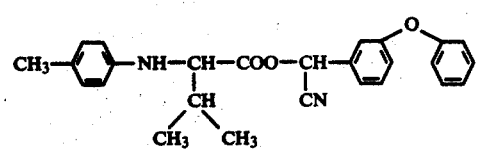

9. Compound according to claim 3 having the formula:

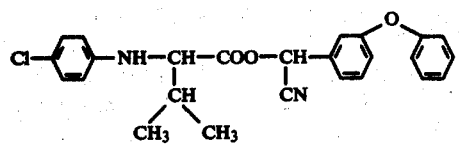

10. Process for producing isovaleric acid ester derivatives of the general formula I:

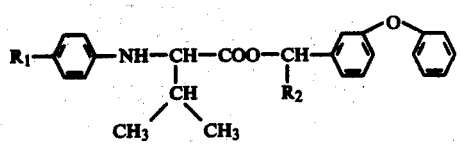

wherein,
 $R_1$ represents hydrogen, methyl group or chlorine atom and
 $R_2$ represents hydrogen or cyano group which process is characterized by reacting a carboxylic acid or a reactive derivative thereof having the general formula IV:

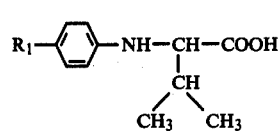

wherein,
 $R_1$ represents the same meaning given above with an alcohol or a reactive derivative thereof having the general formula V:

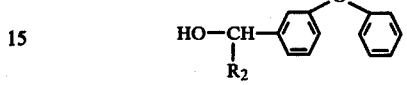

wherein $R_2$ represents the same meaning given above.

11. An insecticidal composition comprising a carrier and as its essential ingredient an insecticidally effective amount of an isovaleric acid ester derivative of the general formula:

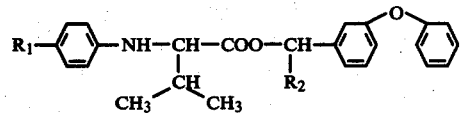

wherein,
 $R_1$ represents hydrogen, a methyl group, or a chlorine atom and
 $R_2$ represents hydrogen or a cyano group.

12. An insecticidal composition according to claim 11 wherein $R_2$ is hydrogen.

13. An insecticidal composition according to claim 11 wherein $R_2$ is a cyano group.

14. An insecticidal composition according to claim 11 wherein $R_1$ is a chlorine atom and $R_2$ is hydrogen.

15. An insecticidal composition according to claim 11 wherein $R_1$ is a methyl group and $R_2$ is hydrogen.

16. An insecticidal composition according to claim 11 wherein $R_1$ is a chlorine atom and $R_2$ is a cyano group.

17. An insecticidal composition according to claim 11 wherein $R_1$ is a methyl group and $R_2$ is a cyano group.

18. An insecticidal composition according to claim 11 which additionally contains a synergist selected from the group consisting of
 (a) N-octylbicycloheptene dicarboxyimide,
 (b) a mixture of N-octylbicycloheptene dicarboxyimide and an alkylarylsulfonic acid salt,
 (c) octachlorodipropylether, and
 (d) pyperonylbutoxide.

19. An insecticidal composition according to claim 18 wherein $R_1$ is a chlorine atom and $R_2$ is a cyano group and the synergist is pyperonyl butoxide.

20. An insecticidal composition according to claim 18 wherein $R_1$ is a methyl group, $R_2$ is a cyano group and the synergist is pyperonyl butoxide.

21. The method of combatting insects which comprises treating the material to be protected with an insecticidally effective amount of an insecticidal composition as set forth in claim 11.

* * * * *

UNITED STATES PATENT OFFICE
CERTIFICATE OF CORRECTION

Patent No. 4,161,537    Dated July 17, 1979

Inventor(s) YOSHIO KATSUDA et al

It is certified that error appears in the above-identified patent and that said Letters Patent are hereby corrected as shown below:

[73]    Assignee:    Dainippon Jochugiku Kabushiki Kaisha, Osaka, Japan

Signed and Sealed this

Thirteenth Day of November 1979

[SEAL]

Attest:

RUTH C. MASON
Attesting Officer

LUTRELLE F. PARKER
Acting Commissioner of Patents and Trademarks

Notice of Adverse Decision in Interference

In Interference No. 100,728, involving Patent No. 4,161,537, Y. Katsuda, M. Nakajima and T. Fujita, INSECTICIDAL ISOVALERIC ACID ESTERS, final judgment adverse to the patentees was rendered Jan. 14, 1983, as to claims 1–17 and 21.

[*Official Gazette May 17, 1983.*]